United States Patent [19]

Lin

[11] Patent Number: 5,581,040
[45] Date of Patent: Dec. 3, 1996

[54] MULTI-FUNCTIONAL HYDRAULIC GRIP

[76] Inventor: Wei-Hwang Lin, 7F-2, No. 95-8 Chang Ping Rd. Sec. 1, Taichung, Taiwan

[21] Appl. No.: 551,407

[22] Filed: Nov. 1, 1995

[51] Int. Cl.$^6$ .................................................. G01N 3/04
[52] U.S. Cl. .................................. 73/857; 73/833; 73/856
[58] Field of Search .............................. 73/831, 832, 833, 73/855, 856, 857, 859, 860

[56] References Cited

U.S. PATENT DOCUMENTS

| | | | |
|---|---|---|---|
| 3,335,603 | 8/1967 | Gram | 73/857 |
| 4,537,080 | 8/1985 | Christiansen | 73/857 |
| 4,721,000 | 1/1988 | Scanlon | 73/857 |
| 5,095,757 | 3/1992 | Larsen et al. | 73/857 |

Primary Examiner—Hezron E. Williams
Assistant Examiner—Max H. Noori

[57] ABSTRACT

A hydraulic grip suitable for use in both tensile and compressive loading of a specimen comprises generally a main body and an outer housing to form a pair of annular chamber thereinbetween. Hydraulic fluid under pressure alternately introduced into the chambers forces the outer housing to move up or downward relative to longitudinal axis of the main body. A cooling circulation may be established between the grip and a compressor so that the testing can be performed in high temperature. This grip also facilitates a rapid replacement of different grip jaws.

4 Claims, 7 Drawing Sheets

MULTI-FUNCTIONAL HYDRAULIC GRIP

BACKGROUND OF THE INVENTION

The present invention relates to specimen grips and more particularly to a multi-functional hydraulic grip which provides rapid assembly or disassembly of the components for facilitating the replacement of the grip jaws thereon and which the hydraulic system has double conduits and is alterable for a cooling system during a specimen testing in high temperature.

Prior art hydraulic specimen grips vary in form and have been advanced as the time being. The most typical specimen grips adapted to tension testing are the horizontal movement, of the jaws relative to the specimen. The jaws have their outward wedge surface in front of the camming surface of an outer gripping housing. Thereby when the outer grip housing is actuated to move vertically by hydraulic pressure, the camming surface moves the jaws horizontally toward each other so as to grip a specimen therebetween. The outer gripping housing may be enclosed or partially opened in order to permit a specimen to be loaded longitudinally or laterally. However. These types of specimen grip have the same disadvantages outlined as follows:

a) They cannot obviate mechanical oscillation because the outer grip housing is urged back up in normal place by springs when the hydraulic pressure is released, especially when some of those springs are weakened because of metallic fatigue that causes unbalanced backward movement.

b) These specimen grips have their jaws slidingly mounted on their laterally protrudent shanks into a T-slot of a mounting body assembly that appears clearances therein, therefore causing unstable movement of the jaws.

c) These specimen grips are operated solely depending on hydraulic pressure via a single conduit without any alteration that presents an operational limit especially when the testing of a specimen is performed in high temperature.

SUMMARY OF THE PRESENT INVENTION

The present invention has a main object to provide a multi-functional hydraulic grip for tensile and compressive testing of specimens which adapts double-conduit hydraulic pressure system for optionally actuating the outer grip housing to move up or downward relative to the-grip jaws.

Further object of the present invention is to provide a multi-functional hydraulic grip which the hydraulic system thereof can be altered for a cooling system when a specimen is tested in high temperature.

Still further object of the present invention is to provide a multi-functional hydraulic grip which the jaws are slidingly mounted into a dovetail groove of a mounting body assembly so as to eliminate the unstability of the jaws.

Still further object of the present invention is to provide a multi-functional hydraulic grip which has an improved swivel joint facilitating to faster connection of various gripping apparatus.

Accordingly, the multi-functional hydraulic grip of the present invention suitable for use in both tensil and compressive loading of specimen is hydraulically actuated and permits transversely clamping the specimen in place between two grip jaws perpendicular to the longitudinal axis of the specimen. The improvement is characterized in that the outer grip housing is actuated by a double-conduit hydraulic pressure system which is under control of a switch valve therebetween to optionally actuate the housing moving up or downward. So that the grip jaws are pressed to move inward toward each other by the interior wall of the housing when it moves upward and the specimen is held without further grip movement during application of the full testing force. The grip jaws are released to separate when the outer grip housing moves downward by adjusting the switch valve to close a second conduit up and to open a first conduit to induce the hydraulic pressure entering into an upper chamber thereof.

Furthermore, this grip can be applied manually without exerting hydraulic force which is alterated into a cooling system when the testing is performed in high temperature.

When the outer clamping housing is removed, the hydraulic grip of the present invention facilitates replacement with other grip apparatus such as a compressive grip. A pair of spiral washers are also provided to adjust the space between the piston and the compressive grip and to enhance the tightness of the grip.

The present invention will become fully understood by reference to the following detailed description thereof when read in conjunction with the art attached drawings.

DETAILED DESCRIPTION OF THE PREFERRED EMBODIMENT

Figure 1:
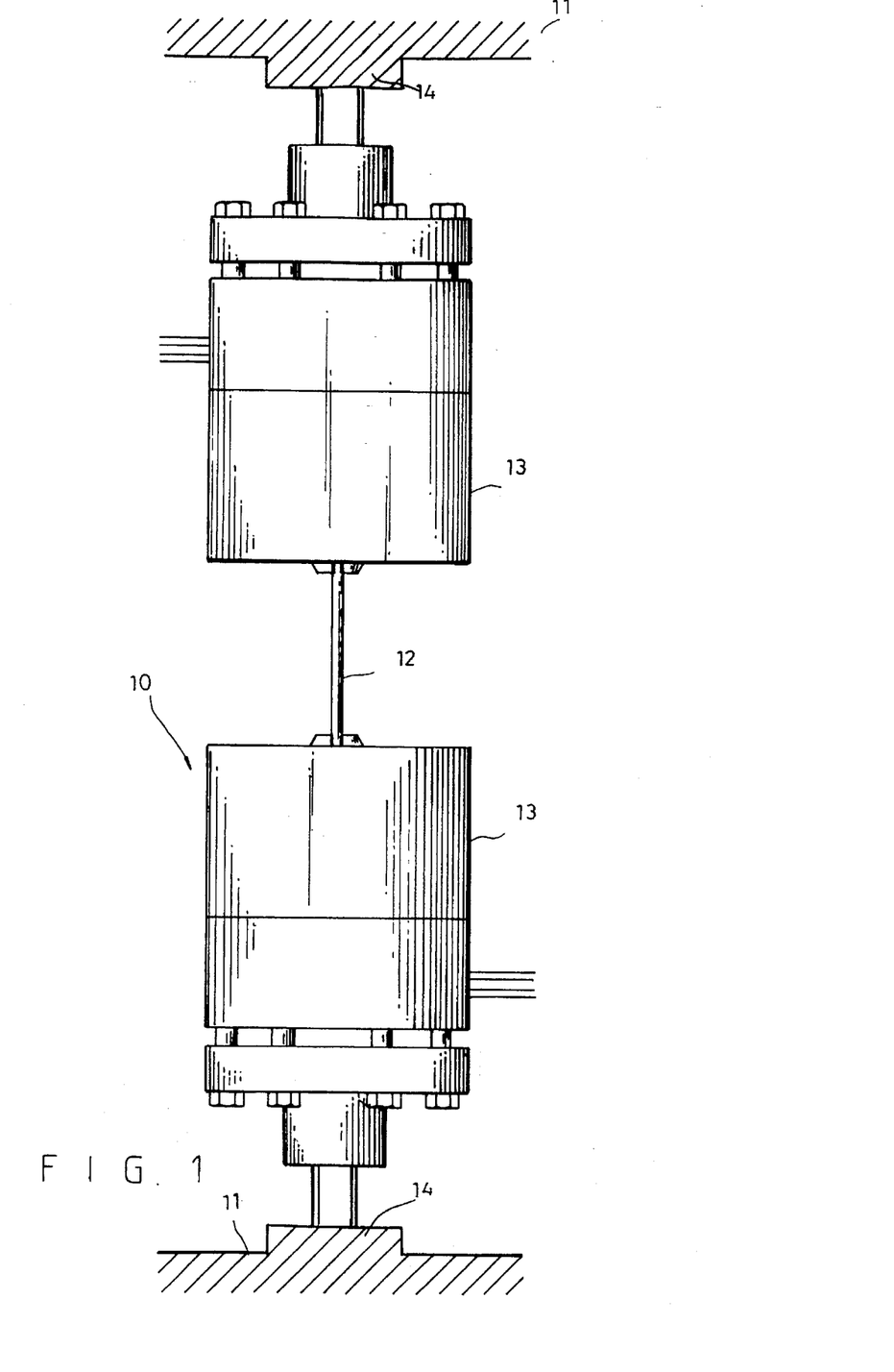
FIG. 1 is a schematic view of a typical testing machine in which the grip of the present invention is utilized.

With reference to FIG. 1, a specimen testing machine illustrated schematically at 10 having a frame 11 which is a conventional load frame commonly used for tensile testing of specimen. The frame has a conventional designed actuator rod or loadcell 14 therein used for applying either a tension load, a compression load, or an alternating tension load and compression load along a longitudinal test axis of a specimen indicated at 12 which is held in a pair of grips 13,13. The grip 13 is attached to the load frame 11 via an actuator rod or loadcell 14 in any suitable manner.

Referring to FIG. 2 to 6 of the drawings, each of the grips 13 is made up to be hydraulically actuated or alternately manually adjusted comprises an upper section 20, a median section 30, a lower section 40 and a grip jaw mounting assembly 50.

Figure 2:
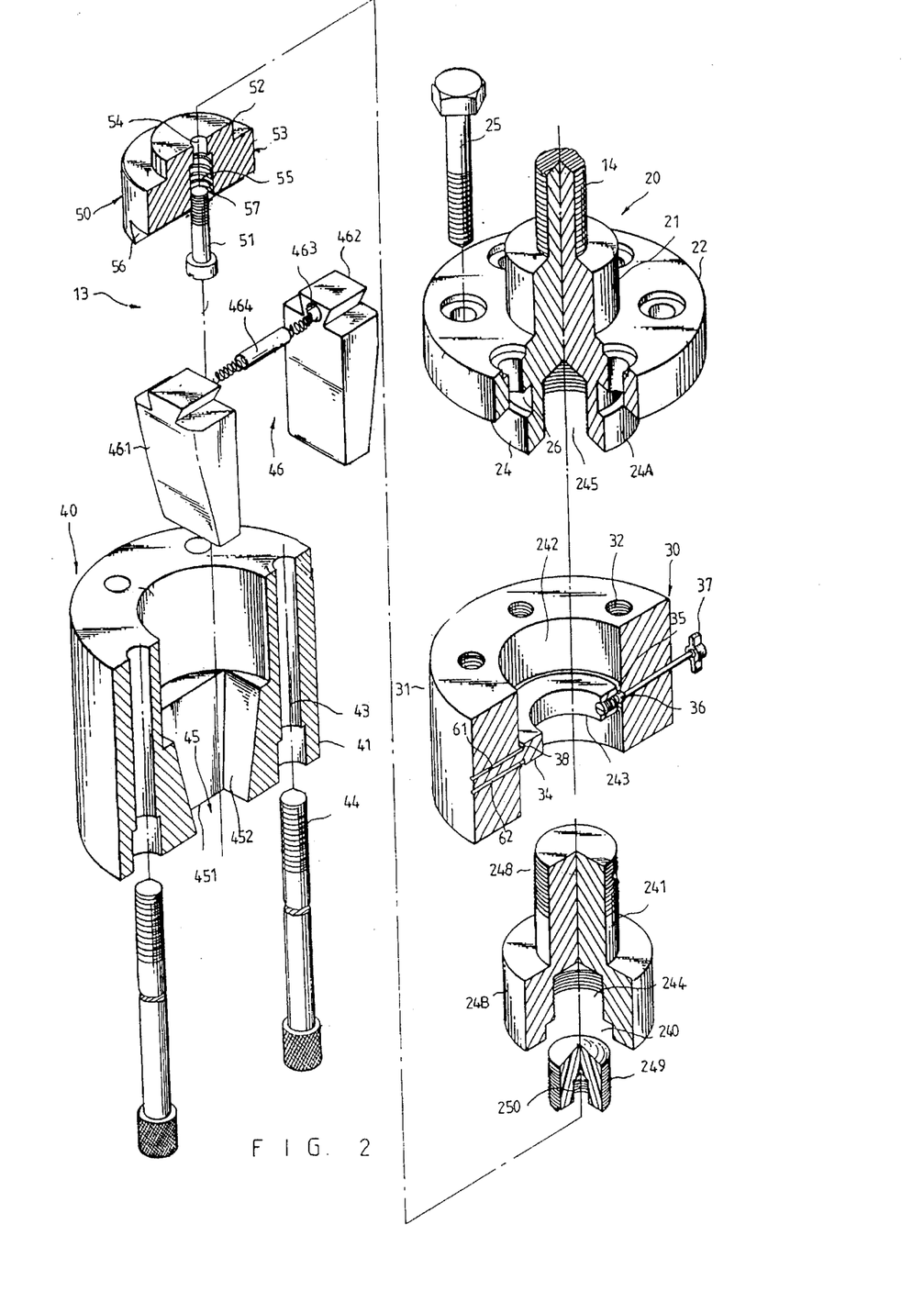
FIG. 2 is an exploded perspective view to show a preferred embodiment of the multi-functional hydraulic grip according to the present invention.

The upper section 20 has a neck 21 screw secured to the actuator rod 14, a circular flange 22 extended transversely from the body including a plurality of vertical screw holes 23 formed spaced apart therearound and a cylinder 24 extended downward from under the flange 22. The cylinder 24 includes an upper portion 24A and lower portion 24B screw connected 248 on a central bore 245 and secured by pin, an annual groove 241 around a less diameter periphery of the lower portion 24B which has a gliding surface will be defined an upper cylinder chamber 242 and a lower cylinder chamber 243 and a threaded central bore 245 in a large diameter recess 244 on the bottom thereof for screw securing an adaptor 249 which has a threaded outer periphery and a less diameter central bore 250 in the bottom in registry with a corresponding central bore 54 of the grip jaws mounting assembly 50 and secured by means of cap screw 51. The mounting assembly 50 further has a larger diameter recess 55 abutting bore 54 for disposing a spring 57 which biases on screw 51 to provide flexibility to obviate the tensile force against the grips.

The median section 30 has a circular wall 31, a plurality of threaded screw holes 32 and 33 formed spaced apart around the rim of each end of the wall 31 and an annular shoulder 34 projected transversely from the inner surface of the wall 31, a first conduit 61 and a second conduit 62 through the wall 31 and communicating with the upper and lower cylinder chambers 242 and 243 respectively. There is also a passage 35 formed on the opposite side of the annular shoulder 34 between the chambers 242 and 243 and a switch valve 36 medially formed in the passage 35. The passage 35 is provided to introduce hydraulic fluid from one chamber to another and the switch valve 36 is normally closed to prevent the hydraulic fluid from passing through and is opened by a handle 37 when a circulation of the hydraulic fluid within the cylinder chambers 242 and 243 and a hydraulic compressor 60 has been established. The annular shoulder has an annular groove 38 on each of it's opposite sides for permitting the hydraulic fluid that may flow smoothly into the chambers 242 and 243 and is sealed with a sealing ring 37. The cylinder 24 is also sealed with a pair of sealing rings 246 and 247 for preventing from leaking hydraulic fluid. Further, the upper section 20 is slidingly secured to the upper rim of the median section 30 by a plurality of cup screws 25. The cup screws 25 are partially threaded on their fore ends. So that a space 26 is defined therebetween for permitting the median section 30 to be slidable on the cylinder 24.

The lower section 40 comprises an outer grip housing 41 which is a cylinder body and has a circular bore 42 on upper portion diametrically equaled to the inner diameter of the median section 30 and plurality of screw holes 43 around the rim thereof formed in registry with those screw holes 33 so that the lower section 40 can be firmly connected with the median section 30 by means of cup screws 44. The lower portion of the outer grip housing 41 has also a taper bore 45 in rectangular form abutting bore 42. The bore 45 includes a pair of upright inner wall 451 and pair of oblique inner wall 452 opposing each other. A pair of grip jaws 46 slidingly mounted to the grip jaw mounting assembly 50. The jaws 46 each has a wedge surface 461 made in registry with the camming surface of the oblique inner walls 452 of bore 45 so as to engage each other, an integral dovetail tang 462 across the width of the bottom thereof and a central cavity 463 on the internal side of the tang 462. The cavity 463 on each of the tangs 462 are provided to anchor a bias means such as a compression spring 464 which tends to separate the jaws 46.

Figure 4:
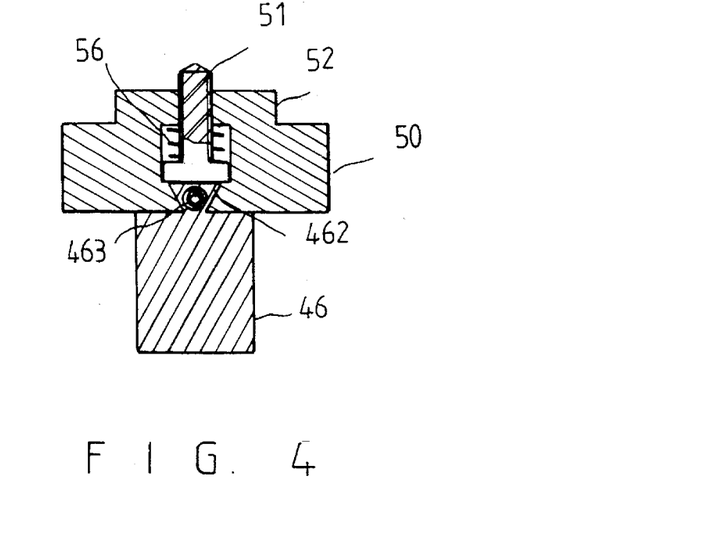
FIG. 4 is a front view to show the grip jaws sliding on a mounting member.

The grip jaws mounting assembly 50 has a dovetail groove 56 across the bottom surface formed in registry with the dovetail tang 462 for slidingly mounting the jaws therein, a less diameter extension 52 on the upper surface made in registry with the circular recess 240 on the lower portion 24B of the cylinder 24, and a threaded central bore 54 longitudinally across the body thereof made in registry with the central bore 250 of the adaptor 249. So that the grip jaws mounting assembly 50 is mounted into the adaptor 249 by a cup screw 51 and biased by spring 57 (as shown in FIG. 4).

The camming surfaces 45 of the outer grip housing 41 substantially engage with the wedge surface 461 of the grip jaws 46. The median section 30 and the lower section 40 are urged in a direction from the cylinder 24 and the grip jaw mounting assembly 50 by hydraulic force induced into the upper chamber 242 via the first conduit 61 when the grip is actuated and the grip jaws 46 are urged apart by the compression spring 464 therebetween. There is a clearance 47 between the grip mounting assembly 50 and the outer grip housing as shown in FIG. 3.

Figure 3:
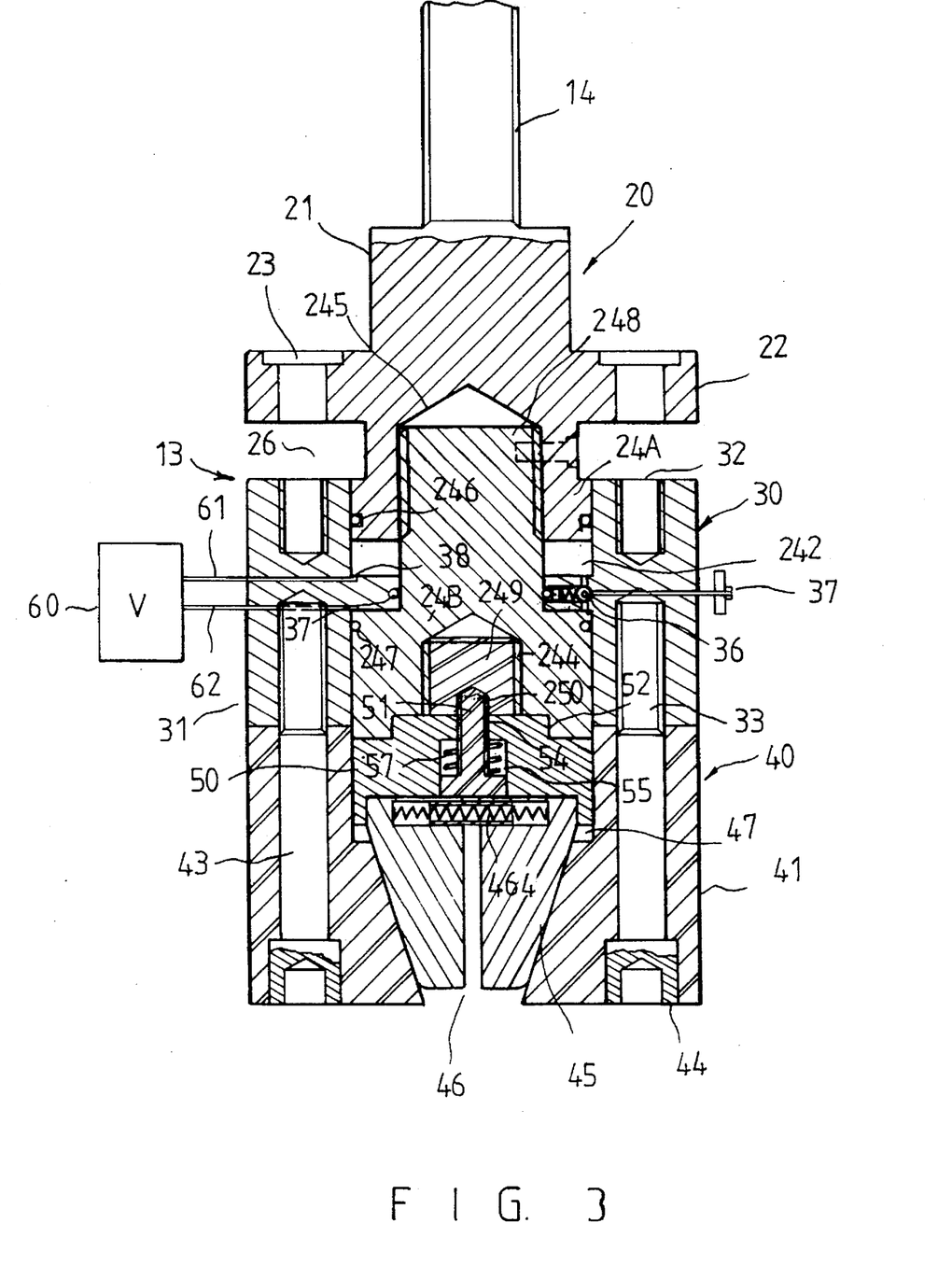
FIG. 3 is a side view to show the preferred embodiment of FIG. 2.

A valve 60 is shown schematically in FIG. 3 which is adapted to alternately control the hydraulic fluid into the grip via the first or second conduit 61 or 62. If a specimen is to be loaded, the valve 60 will turn to close the second conduit 62 and open the first conduit 61 supplying sufficient hydraulic fluid into the upper cylinder chamber 242. This hydraulic pressure acts between the upper wall of the upper cylinder chamber 242 and the upper surface of the annular shoulder 34 to force the median section 30 in addition to the lower section 40 downwardly relative to the grip jaw mounting assembly 50 and the grip jaws 46 are urged apart by the compression spring 464. When the specimen has been slid in place between the jaw gripping surfaces, the valve 60 will turn reversely to release the hydraulic fluid from inside the upper cylinder chamber 242 and to supply sufficient hydraulic fluid via the second conduit 62 into the lower cylinder chamber 243 so as to force the median section 30 in addition to the lower section 40 upwardly. In turn, the camming surfaces 452 of the outer grip housing 41 acting on the wedge surfaces 461 of the jaws 46 tend to move the jaws 46 horizontally toward each other. The specimen is gradually gripped where the space 26 and the clearance 47 are reduced to a predetermined extent. Since a high enough pressure, the gripping action and the clamping force of the jaws 46 become sufficiently high to preload the grip to a point where there is virtually no change in grip force nor relative movement between the jaws 46 and the surfaces 452 when the actuator is operated for loading the specimen. The relative axial movement between the specimen and the grip is virtually eliminated because the horizontal movement of the jaws riding on the lower surface of the jaw mounting assembly 50. Beside, there is a constant preload or constant clamping force on the specimen so that the specimen loading does not change during testing.

In addition, by employing hydraulic force instead the springs to urge the outer grip housing downwardly will insure the reliability as well as the durability of the grip.

Figure 5:
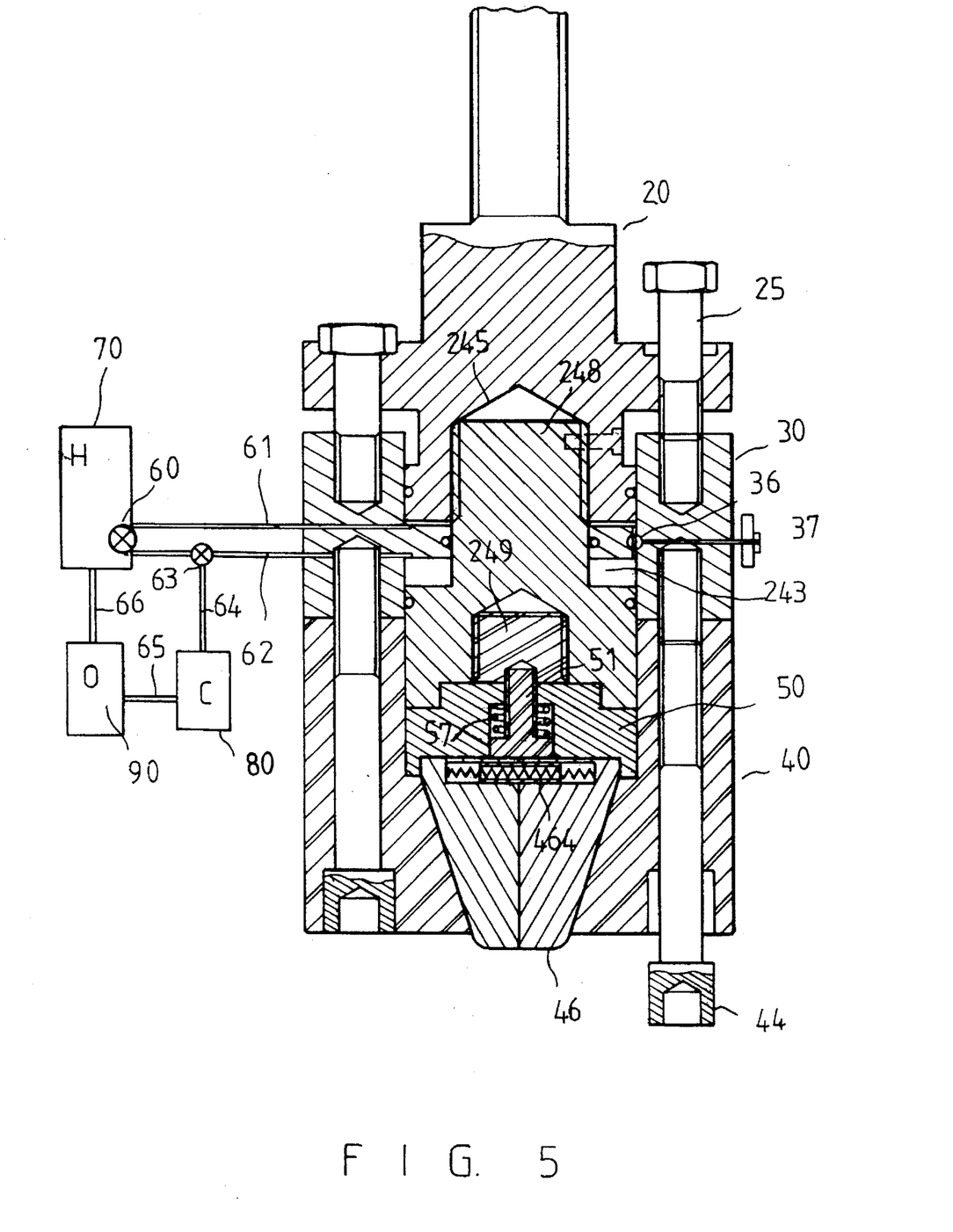
FIG. 5 is sectional view to indicate that the grip jaws are in closed position.

Referring to FIG. 5, an alternative arrangement of the conduits is schematically indicated at the left side of the grip, which shows the first and second conduits 61 and 62 are connected between the grip and a hydraulic compressor 70, a valve 60 in the compressor 70 alternately controlling hydraulic fluid between the conduits 61 and 62, a three way valve 63 added to the second conduit 62 to perpendicularly connected a third conduit 64 which induces the hydraulic fluid into a cooling system 80, a fourth conduit 65 between the cooling system and an oil tank 90 provided for inducing the hydraulic fluid from the cooling system 80 into the oil tank 90 and a fifth conduit 60 connected between the oil tank 90 and the compressor 70 for replenishing oil into the compressor 70.

Upon this arrangement, when opens the valve 36 on the passage 35 by swinging the handle 37 and adjusts valve 60 to permit the hydraulic fluid flowing out through the first conduit 61 into the upper cylinder chamber 242 and in turn into the lower cylinder chamber 243 via passage 35 and then flowing back to the compressor 70 via the second conduit 243. So that hydraulic pressures in the two chambers 242 and 243 are balanced and a circulation of hydraulic fluid within the compressor 70 and the grip is therefore established. If the three way valve 63 is turned to block the hydraulic fluid from directly flowing back to the compressor 70 and permits the fluid entering into the cooling system 80 via the third conduit 64 at first and then flows back via the fourth conduit 65, the oil tank 90 and the fifth conduit 66 that a circulation of hydraulic fluid in addition to a cooling system is thus constructed.

Based on this modification, the testing can be performed in a high temperature. In this mode, the gripping activity has to be manually operated by fastening or loosening the cup screws 25 because there is flexible space in the bottom of each threaded screw hole 32 for facilitating such adjustment.

Figure 6:
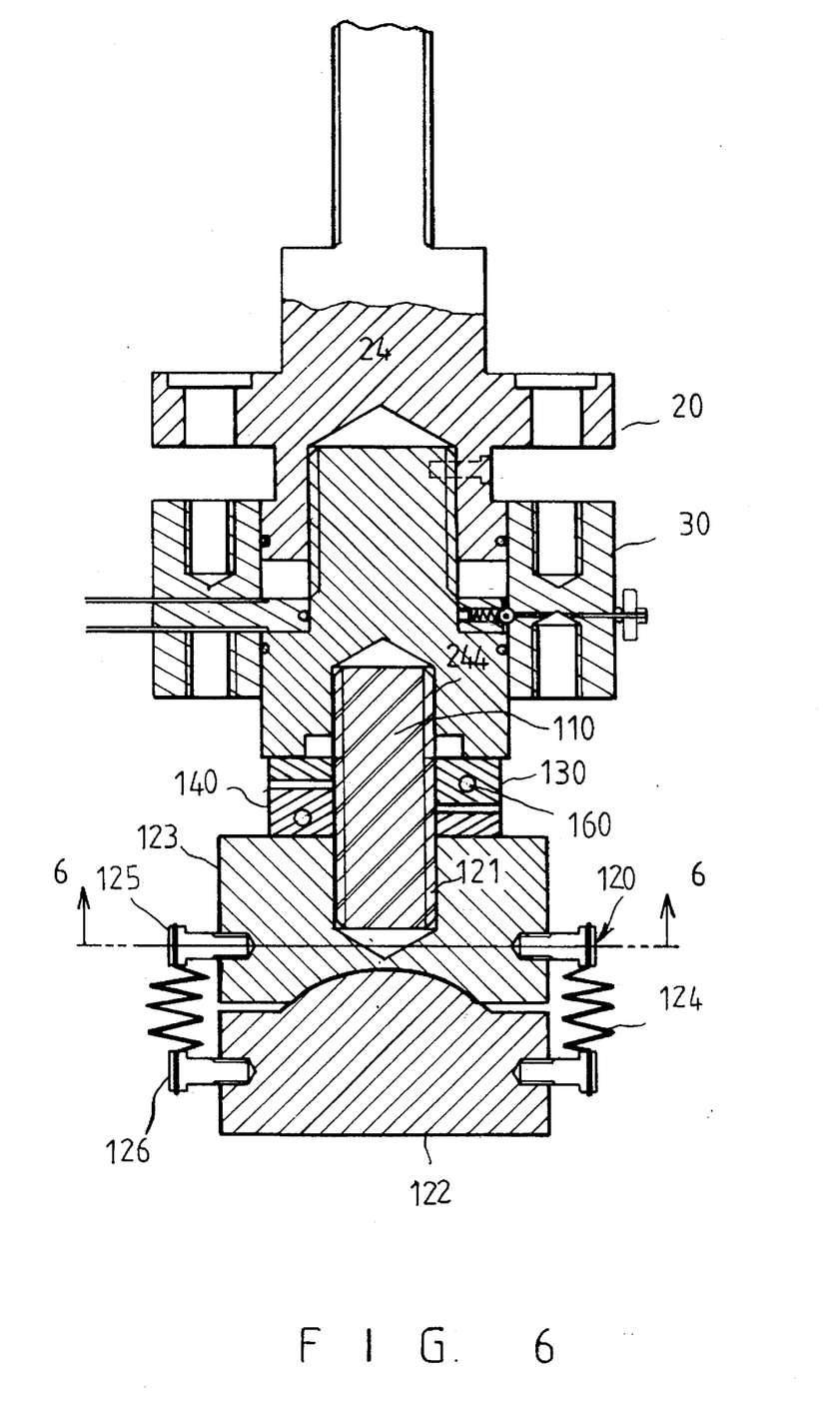
FIG. 6 is a sectional view to show an alternative embodiment of the present invention.
Figure 7:
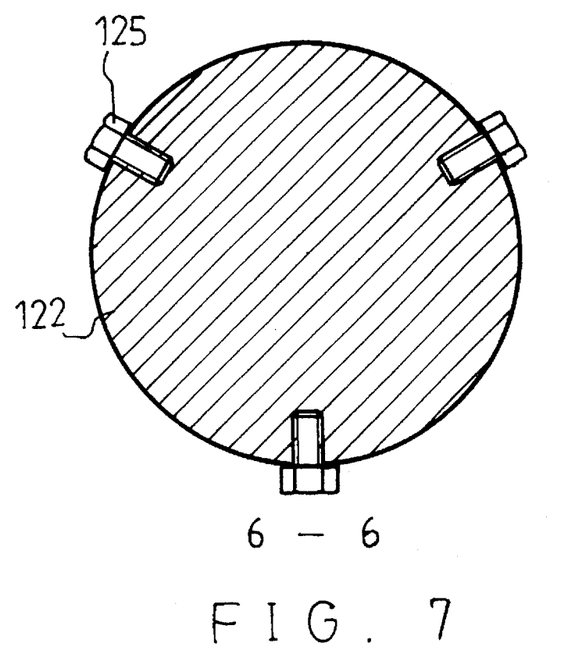
FIG. 7 is a sectional view taken on line A—A in FIG. 6.
Figure 8:
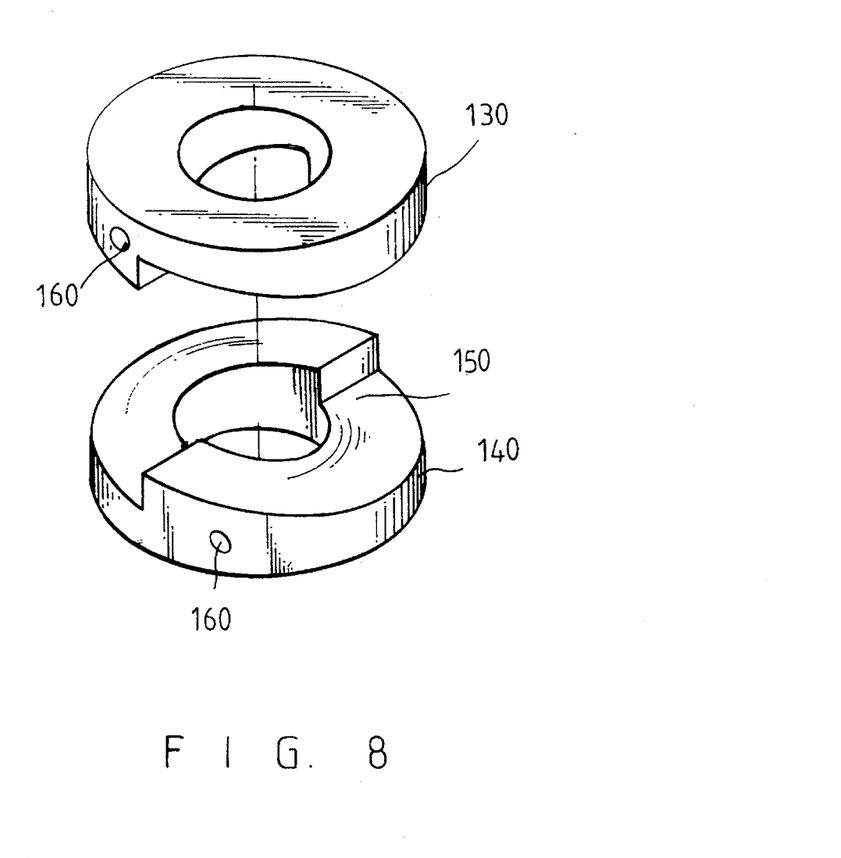
FIG. 8 is an exploded perspective view to show the spiral washers of FIG. 6.

Referring to FIGS. 6, 7 and 8, an alternative embodiment of the present invention is shown. In this embodiment, the general function and structure of the specimen grip 100 is mostly similar to the specimen grip illustrated in FIGS. 1 to 3 and the above discussion is equally applicable to grip 100 in the most instances.

The lower section 40, the grip mounting assembly 50 including the grip jaws 46 in the above embodiment are now removed in grip 100. Instead of is a shaft 110 which has threads on outer periphery with one end threaded into the threaded central bore 244 of the cylinder 24 and the other end threaded into a threaded central recess 121 of a compression grip 120. The compression grip 126 is composed of a male spherical grip jaw 122 and a female grip spherical jaw 123 axially connected by a plurality of springs 124 in the manner as shown in FIG. 7. Each of the grip jaws 122 and 123 has three screws 125 and 126 spacedly and transversely secured to their outer peripheries and each pair of the respective screws 125 and 126 are suspended by a spring 124 therebetween so that the gripping force between the two spherical grip jaws 122 and 123 is average. A pair of spiral washers 130 and 140 axially mounted to the shaft 110 between the cylinder 24 and the compression grip 120. The spiral washers 130 and 140 each has a spiral surface 150 toward each other and a plurality of transverse recesses 160 formed spaced apart around the outer periphery thereof for facilitating a minute adjustment (as shown in FIG. 8). The space between the spiral washers 130 and 140 is variable by swinging either washer 130 or washer 140 clockwise or counterclockwise up to 180 degrees on the shaft 110. So that this spiral washers 130 and 140 are provided to tighten the compression grip 120 and ensure the preload without inducing offsets in the load train.

Since the cup screws 44 are taken out and the lower section 40 is removable. This permits the grip jaws 46 or the grip jaw mounting assembly 50 to be removed out of cylinder 24 as discussed above. Therefore, if different jaws are to be replaced, it will be done quickly and easily.

Note that the specification relating to the above embodiments should be construed as to exemplary rather than as limitative of the present invention, with many variations and modifications being readily attainable by a person of average skill in the art without departing from the spirit or scope thereof as defined by the appended claims and their legal equivalents.

I claim:

1. A multi-function hydraulic grip adapted to be used in both tensile and compressive loading of a specimen comprising:

a main body of hollow interior having three sections axially connected together and a cylinder member slidably secured therein;

a pair of first and second conduits disposed parallel into a peripheral wall of a median section of said body that communicate respectively with a first and a second annular chambers;

a passage longitudinally formed on an annular shoulder opposite to said conduits to communicate to said annular chambers;

Valve means for permitting or blocking a hydraulic fluid from passing through said chambers disposed within said passage and switch means to operate the said valve;

an adaptor screw secured into a stepped central bore in lower end of said cylinder member movable in concert therewith, said adaptor having a threaded outer periphery and a threaded less diameter central bore in the bottom for screw securing, and a circular member having less diameter portion integrated on upper surface to define a dovetail slide for permitting a pair of grip jaws slid thereabout, and fit to an enlarged recess of the said less diameter central bore of the said cylinder.

2. A grip as claimed in claim 1, wherein said grip jaws each has a dovetail tang made in registry with the dovetail slide of said circular member.

3. A grip as claimed in claim 1, further comprises a third conduit connected between a second conduit and a cooling system via a three way valve on said second conduit, a fourth conduit connected between said cooling system and an oil tank and a fifth conduit connected between said oil tank and a compressor which connects to both said first and second conduits and is operated by a control valve.

4. A grip as claimed in claim 1, further has a threaded axle rod for shifting different grips jaws, said threaded axle rod being engageable with the threaded central bore of said cylinder and said different grips jaws.

\* \* \* \* \*